(12) United States Patent
Frantz et al.

(10) Patent No.: US 12,026,897 B2
(45) Date of Patent: Jul. 2, 2024

(54) AUGMENTED REALITY SYSTEM, AN AUGMENTED REALITY HMD, AN AUGMENTED REALITY METHOD AND A COMPUTER PROGRAM

(71) Applicants: IMEC VZW, Leuven (BE); Vrije Universiteit Brussell, Brussels (BE)

(72) Inventors: Taylor Frantz, Asse (BE); Bart Jansen, Mechelen (BE); Jef Vandemeulebroucke, Ganshoren (BE); Frederick Van Gestel, Ghent (BE); Johnny Duerinck, Zellik (BE); Thierry Scheerlinck, Grez-Doiceau (BE)

(73) Assignees: IMEC VZW (BE); Vrije Universiteit Brussell (BE)

( * ) Notice: Subject to any disclaimer, the term of this patent is extended or adjusted under 35 U.S.C. 154(b) by 0 days.

(21) Appl. No.: 18/259,374

(22) PCT Filed: Oct. 6, 2021

(86) PCT No.: PCT/EP2021/077631
§ 371 (c)(1),
(2) Date: Jun. 26, 2023

(87) PCT Pub. No.: WO2022/144116
PCT Pub. Date: Jul. 7, 2022

(65) Prior Publication Data
US 2024/0062387 A1 Feb. 22, 2024

Related U.S. Application Data

(60) Provisional application No. 63/176,974, filed on Apr. 20, 2021, provisional application No. 63/132,907, filed on Dec. 31, 2020.

(51) Int. Cl.
*G06F 3/00* (2006.01)
*A61B 34/20* (2016.01)
(Continued)

(52) U.S. Cl.
CPC .............. *G06T 7/246* (2017.01); *A61B 34/20* (2016.02); *A61B 90/37* (2016.02);
(Continued)

(58) Field of Classification Search
CPC ...... A61B 2034/2055; A61B 2090/365; A61B 34/20; A61B 90/37; G02B 2027/0138;
(Continued)

(56) References Cited

U.S. PATENT DOCUMENTS

2019/0042834 A1* 2/2019 Gavino ................ G06V 10/454
2019/0385342 A1* 12/2019 Freeman ................ G06T 11/00
2020/0197107 A1 6/2020 Ryan et al.

OTHER PUBLICATIONS

Unberath et al. "Augmented reality-based feedback for technician-in-the-loop C-arm repositioning," Jun. 22, 2018, https://arxiv.org/pdf/1806.08814.pdf pp. 1-6.
(Continued)

*Primary Examiner* — Insa Sadio

(57) ABSTRACT

Augmented reality method comprising: receiving continuously from a SLAM system in an HMD SLAM data and performing a SLAM tracking; performing an IR object tracking comprising at each IR iteration of the IR object tracking; and displaying at each IR iteration an AR visualization on an AR display in the HMD such that the AR visualization appears on an AR position or an AR pose in the world coordinate system depending on the pose of the object in the world coordinate system of the current IR iteration.

20 Claims, 3 Drawing Sheets

(51) Int. Cl.
| | |
|---|---|
| *A61B 90/00* | (2016.01) |
| *G02B 27/00* | (2006.01) |
| *G02B 27/01* | (2006.01) |
| *G06F 3/01* | (2006.01) |
| *G06T 7/246* | (2017.01) |
| *G06T 7/73* | (2017.01) |
| *G06T 19/00* | (2011.01) |

(52) U.S. Cl.
CPC ..... *G02B 27/0093* (2013.01); *G02B 27/0172* (2013.01); *G06F 3/012* (2013.01); *G06T 7/73* (2017.01); *G06T 19/00* (2013.01); *A61B 2034/2055* (2016.02); *A61B 2090/365* (2016.02); *G02B 2027/0138* (2013.01); *G02B 2027/014* (2013.01); *G02B 2027/0141* (2013.01); *G06T 2207/10048* (2013.01); *G06T 2207/30004* (2013.01); *G06T 2207/30196* (2013.01); *G06T 2207/30204* (2013.01); *G06T 2207/30244* (2013.01)

(58) Field of Classification Search
CPC ...... G02B 2027/014; G02B 2027/0141; G02B 27/0093; G02B 27/0172; G06F 3/012; G06T 19/00; G06T 2207/10048; G06T 2207/30004; G06T 2207/30196; G06T 2207/30204; G06T 2207/30244; G06T 7/246; G06T 7/73
See application file for complete search history.

(56) References Cited

OTHER PUBLICATIONS

Qian et al. "ARssist: augmented reality on a head-mounted display for the first assistant in robotic surgery," Heathcare Technology Letters, vol. 5, No. 5. Sep. 17, 2018, pp. 194-200.

Fotouhi et al. "Interactive Flying Frustums (IFFs): spatially aware of surgical data visualization," International J. of Computer Assisted Radiology & Surgery, Springer, DE, vol. 14, No. 6. Mar. 12, 2019, pp. 913-922.

Andress et al. "On-the-fly augmented reality for orthopedic surgery using a multimodel fiducial," J. of Medical Imaging, Society of Photo-Optical Instrumentation Engineers, vol. 5. No. 2, Jan. 26, 2018, p. 21209.

International Search Report for International Application No. PCT/EP2021/077631 dated Jan. 14, 2022 (3 pages).

* cited by examiner

Fig. 4A                    Fig. 4B

AUGMENTED REALITY SYSTEM, AN AUGMENTED REALITY HMD, AN AUGMENTED REALITY METHOD AND A COMPUTER PROGRAM

CROSS-REFERENCE TO RELATED APPLICATIONS

This application is a National Stage of PCT/EP2021/077631 filed Oct. 6, 2021, which claims the benefit of U.S. Provisional Application No. 63/176,974, filed Apr. 20, 2021, and U.S. Provisional Application No. 63/132,907, filed Dec. 31, 2020, and which applications are incorporated herein by reference in their entireties. To the extent appropriate a claim of priority is made to each of the above-recited applications.

TECHNICAL FIELD

The present invention relates to an augmented reality system, an augmented reality HMD, an augmented reality method and a computer program.

PRIOR ART

Visual imagery can provide assistance to medical professionals (e.g., doctors, surgeons, etc.) during various surgical procedures and/or for evaluation or diagnosis. Surgical navigation allows to display prior imaging (CT, MRI, etc.) and surgical planning during the intervention. In some examples, the medical imagery may be spatially referenced to a tracking object, such as a ruler, a pin, or implant, etc. Conventional imaging solutions include external tracking devices and wall-mounted displays that may provide two-dimensional multi-planar reconstructions. Additionally, augmented reality images, which may augment an individual's view with various information, can currently be provided by way of wall-mounted screens or in a display of a surgical microscope. Augmented reality head-mountable devices have been utilized in the medical field, but conventional systems make use of visible light cameras and known natural feature descriptor tags. Such solutions can be negatively affected by changes in lighting and/or field of view. Accordingly, more reliable systems, devices, and methods are desired for utilization in augmented reality, head-mountable medical device applications.

There are many different tracking algorithms and methods which can be used in augmented reality head-mountable devices and each of them have their advantage and disadvantage.

Some off-the-shelf augmented head-mountable devices (short: HMD) sense the dimensions of the surrounding environment and localize the HMD with respect to that environment, using an approach called Simultaneous Localization and Mapping (SLAM). The result is an estimation of position and pose of the augmented head-mountable device in the environment, i.e. in the world coordinate system. Any augmented content can be displayed in the HMD in the correct position with respect to the environment. This is achieved normally by one or more sensors on the augmented head-mounted device like one or two cameras (grey scale or RGB), time of flight cameras, Inertial Measurement Unit (IMU), etc.). This approach does not require markers nor prior calibration or registration. The advantage of the SLAM is that it provides the position of the HMD in the environment with a low latency so that the augmented reality content fixed in the world coordinate system can be shown stable even when the HMD is moving. The problem of this approach is that the errors accumulate with the time and the accuracy of the detection is limited. Normally, the precision of such SLAM approaches is in the region of one or more centimeters (cm) which is not sufficient for medical purposes.

WO2020/109903 discloses an HMD for medical purposes. It uses infrared (IR) marker tracking for detecting patient and/or tools (subsequently short object) in the environment. The HMD comprises an IR camera and the object to be detected includes a number of IR markers. The HMD can determine the pose of the object from the 2D image and determine thus the position of the object with respect to the HMD or with respect to each other. This method provides a higher accuracy the above-mentioned SLAM approach. However, it has the disadvantage that the latency is much higher, and the augmented reality content related to the position of the detected object can jump which is disturbing as well for medical applications. In addition, this approach has the advantage that when the IR markers are not in the image of the IR camera anymore, it will take a while to retrieve the correct position of the object, when the IR markers come back into the field of view of the IR camera. This is for example the case, when the surgeon quickly turns the head away from the patient and back. For this reason, it is disclosed a second IR tracking mechanism which is fixedly installed in world coordinate system to keep the position of the object tracked, even when not in the field of view of the IR camera of the HMD. However, this means again additional equipment to be installed in the operation room.

Kunz et al discloses in the article "Infrared marker tracking with the HoloLens for neurosurgical interventions" published in the Journal Current Direction in Biomedical Engineering on Sep. 17, 2020 to detect the 3D positions of the IR markers using a time-of-flight camera. This obviously reduces the latency, because the computational expensive transformation from the 2D IR points into the 3D positions of the IR marker is replaced by simply taking the 3D positions measured by the time-of-flight camera at the 2D IR points recorded with the IR camera. But this goes again on the cost of the accuracy as the precision of the time-of-flight camera is not sufficient for medical operations.

There are many more existing tracking methods like with stereo RGB or greyscale cameras, monocular RGB or greyscale cameras, time-of-flight cameras, and many more. All of these tracking methods have their advantage and their disadvantage. Unfortunately, all existing HMD solutions for medical purposes are complex, expensive and require often the additional installation of equipment in the environment. All simple solutions proposed for solving this problem have failed to fulfil the challenging requirements in precision, latency and failsafe for medical applications.

BRIEF SUMMARY OF THE INVENTION

It is the object of the invention to provide an HMD which overcomes the problems of the state of the art, which is suitable for the challenging requirements of medical applications and/or which is computationally efficient.

According to the invention, this object is solved by the augmented reality system, the augmented reality method, the HMD and the computer program according to the independent claims.

By updating the display of the AR visualization at the AR position/pose in the world coordinate system based on the pose of the object in the world coordinate system using the IR object tracking and based on the HMD pose of the SLAM tracking, the disadvantages of both methods are compensated. Especially, by updating the display of the AR visualization between two subsequent IR iterations by the HMD pose of the SLAM tracking, the AR visualization is displayed with a low latency. Since the AR visualization is updated every IR iteration by the pose of the object from the precise IR object detection, the AR visualization can be displayed with a high precision. Due to the small time between two subsequent IR iterations, the drift error of the SLAM algorithm has no time to accumulate to become significant. This way, the precision of the IR object tracking can be combined with the low latency of the SLAM algorithm without any disadvantages.

The dependent claims refer to further advantageous embodiments.

Distinguishing two types of correspondence finding algorithms depending on the presence of a prior pose of the object of a prior IR iteration, allows to accelerate remarkably the pose detection, when a prior pose of the object is available.

When a prior pose of the object is available from a recent prior IR iteration, a Hungarian assignment algorithm based on the distance between the 2D positions of the IR object markers of the IR image of the current IR iteration and the 2D positions of the IR object markers in the IR image of the prior IR iteration is used. This algorithm finds at low computational cost the correspondence quickly.

When no prior pose of the object is available from a recent prior IR iteration, normally a time consuming and power intensive object pose detection algorithm needs to be performed. The inventors found a very efficient algorithm which is fast and reliable. This algorithm uses only a predetermined (optimal) sub-set of three IR object markers to detect the correspondence between the IR object markers in the IR image and the IR object markers of the set of IR object markers. This accelerates the initialization (e.g. when starting the method) or re-initialization (e.g. when looking away from the objects to be detected and back to the objects) of the object detection significantly and avoids thus annoying waiting times to start or re-start the AR visualization.

The fitting of the form of the IR object marker on a contour of high intensity pixel groups detected in the IR image allows to detect IR object markers in the IR image with low false positive rate and to determine their 2D position with a high precision.

Especially, by arranging the complete processing in the HMD, i.e. on-board, the HMD is a stand-alone system which does not require any further equipment in the operation room. This facilitates the use in and outside of the operation room. Due to the efficient algorithms described above, the present method can be applied as on-board system on a commercially available HMD.

Other embodiments according to the present invention are mentioned in the appended claims, the subsequent description of

BRIEF DESCRIPTION OF THE DRAWINGS

FIG. 4A shows a raw IR image taken from the infrared sensor of the HMD showing the object to be detected.

FIG. 4B shows a processed IR image for detecting the IR object markers.

In the drawings, the same reference numbers have been allocated to the same or analogue element.

DETAILED DESCRIPTION OF AN EMBODIMENT OF THE INVENTION

Other characteristics and advantages of the present invention will be derived from the non-limitative following description, and by making reference to the drawings and the examples.

Figure 1:
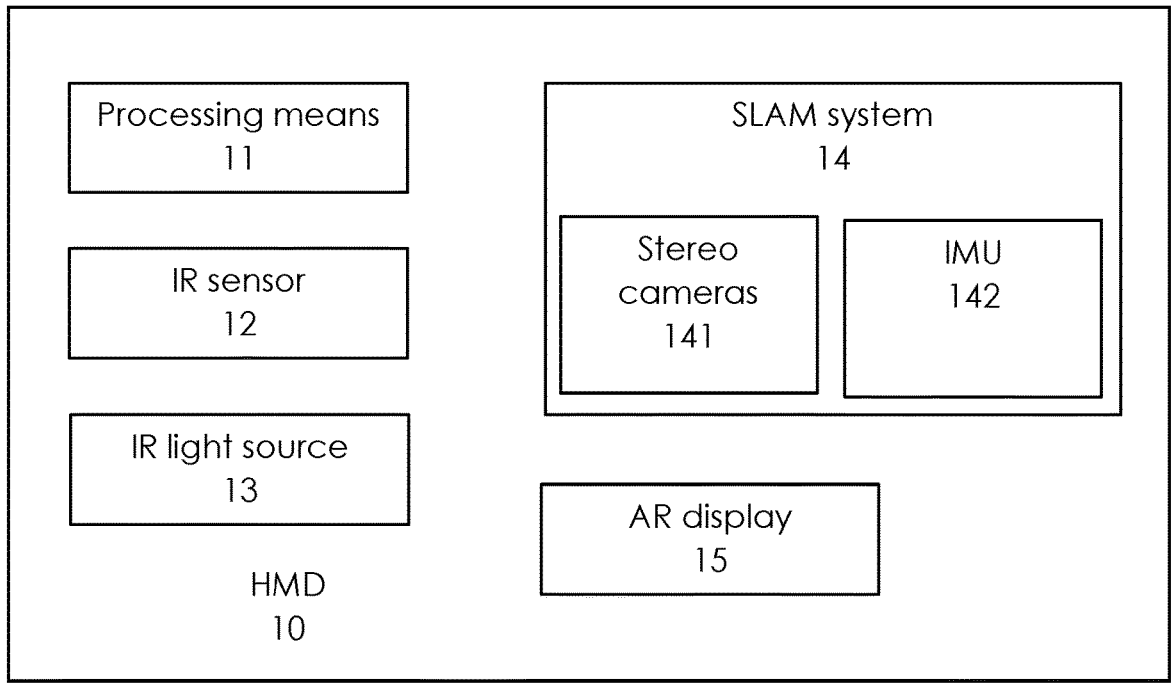
FIG. 1 shows a schematic diagram of an embodiment of the HMD according to the invention.

FIG. 1 shows an embodiment of the HMD 10. The HMD is a head-mountable device with augmented reality (AR) functions. That is that the HMD 10 allows to overlay AR visualizations over the real environment as seen by the user wearing the HMD 10 such that the user sees the reality augmented with the AR visualization. The HMD 10 is particularly configured for medical interventions, in particular configured for surgical operations. The HMD 10 is configured preferably to augment the view of a medical person with respect to a patient. The HMD 10 is preferably configured to augment the view of the medical person for a special medical intervention for which the intervention specific information is shown in the AR display of the HMD 10 at an AR pose/position depending on the pose of the patient and/or of a medical tool. Using an HMD, the structures of interest (lesions, critical structures, cutting lines, etc.) can be visualized in the surgical/medical view; i.e. aligned with the patient using 3D rendering, overlaid with the actual patient structures. This can provide a more intuitive visualization, effectively giving the physician "X-ray" vision. It reduces the cognitive load for the surgeon, by avoiding having to dynamically translate a visualization displayed elsewhere (e.g., on a wall-mounted display) to the actual patient view.

The HMD 10 comprises a processing means 11, an infrared (IR) sensor 12, a SLAM system 14 and an AR display 15.

The processing means 11 is configured to execute the subsequently described methods/algorithms according to the invention. The processing means 11 comprises preferably a general processing means like a CPU or programmable microprocessor. Preferably, the processing means 11 comprises a programmable processor. Preferably, the subsequently described functions/methods/algorithms of the invention are realized as software programs executed on the processing means 11 or in the processor. However, in a less preferred embodiment, the functions can also be realized by a function specific microprocessor. Preferably, the processing means 11 is arranged in the HMD 10. This means that the complete processing necessary for the inventive functions is performed on-board, i.e. in the HMD 10. Thus, the HMD 10 can be used everywhere, and it is not necessary to install other equipment. This is very challenging, because the computational effort of real-time high precision pose detection as necessary for medical purposes exceeds the capacity of most HMDs 10. Thus, special custom HMDs 10 are necessary with high computational processors and a high-power consumption. The subsequently proposed method allows to perform the detection fully on-board even when using conventional processing capacities. The function of the processing means 11 will be described subsequently, when describing the method of the invention. Without repeating this explicitly, the processing means 11 is configured to perform the subsequently described functions. The processing means 11 is preferably a single processor 11. However, it is also possible that the processing means 11 is distributed over several processing sub-means. For example, the SLAM processing could be integrated into a SLAM chip of the SLAM system. A part of the IR image processing could be integrated in the IR sensor 12. Even if it is preferred that all the processing is done in the HMD 10, i.e. that the full processing means 11 is integrated in the HMD 10, it is also possible to arrange a part or the complete processing means 11 outside of the HMD 10. The processing means 11 or the HMD 10 comprises preferably a storage for storing the software programs according to the invention to be executed on the HMD 10. The storage stores preferably further a library of objects and associated to each object the spatial relationship of the set of object markers 21 as arranged on the object 20.

The IR sensor 12 is configured to capture an IR image of the environment of the HMD 10. The IR sensor 12 is preferably an IR camera 12. When the HMD 10 is worn by a user, the optical axis of the IR sensor 12 is preferably arranged in substantially the same direction as the optical axis of the eyes of the user (not considering a possible off-set). Thus, the IR sensor 12 captures an IR image of the environment, which is seen by the user, when wearing the HMD 10. The IR image detects light in the IR spectrum. In other words, the IR sensor 12 points in the direction of view of the HMD 10. In particular, the IR sensor 12 is configured to detect light in the spectral range in which the object markers emit light and/or in which an IR light source of the HMD 10 emits light. The IR sensor 12 has preferably an angle of view of more than 90°, preferably of more than 100°, preferably of more than 110°, preferably of more than 120°. The IR sensor 12 or IR camera 12 can be modelled, for example as a pin hole camera. The model of the IR sensor 12 is stored in the HMD 10 for further processing. The model of the IR sensor 12 allows to compute the position of a 3D point in the IR sensor coordinate system into its corresponding 2D point in the image taken by the IR sensor 12. The model of the IR sensor 12 is sometimes also called the sensor intrinsic transform. The IR sensor coordinate system corresponds to the coordinate system of the IR sensor 12. The IR sensor coordinate system has preferably its origin in the IR camera 12. If the IR sensor coordinate system is not identical to a main HMD coordinate system used in the HMD, a sensor extrinsic transform can be used to transform the coordinates of the IR sensor coordinate system into the other main HMD coordinate system. The HMD 10 has preferably only one IR camera 12. However, the inventive method can also be used on HMD 10 having more than one IR camera, like a stereo IR camera with two IR cameras.

In a preferred embodiment, the HMD 10 comprises an IR light source 13 emitting IR light in the spectral range of the IR sensor 12. This allows to detect IR reflective object markers by illuminating them with the IR light source 13 and detecting in the IR image taken by the IR sensor 12 the object markers reflecting the IR light from the IR source 13. The IR light source emits the IR light also in the direction of view of the HMD 10. In a less preferred embodiment, it would also be possible to arrange the IR light source 13 in the environment to illuminate the markers 21. If the markers 21 emit actively IR light, the IR light source 13 can be completely avoided.

The SLAM system 14 comprises one or more sensors configured to sense SLAM data. SLAM data are the data of the environment of the HMD 10 and/or of the movement of the HMD 10 used for the SLAM algorithm. The SLAM data is preferably a combination of inertial measurement data for the movement of the HMD 10 and image data of the environment of the HMD 10. The image data can be one or more of RGB camera images, grey scale camera images, stereo (RGB/greyscale) camera images, 3D camera images (also called time of flight camera images) or any other. The IR sensor 12 could be in some embodiments part of the SLAM system 14. However, preferably, the SLAM algorithm is not based on the IR images. Preferably, a system of stereo greyscale cameras 141 is used to obtain a 3D map of the environment. The inertial measurement data are preferably obtained by an inertial measurement unit (IMU) 142 recording the translational and orientational movement of the HMD (in 6 degrees of freedom). Thus, the IMU 142 comprises preferably an accelerometer measuring the acceleration in 3 degrees of freedom and a gyroscope measuring the rotational acceleration in 3 degrees of freedom. Preferably, the IMU 142 registers as well the magnetic direction with a magnetometer. However, it is also possible that the SLAM algorithm uses a different type of SLAM data and uses corresponding different SLAM sensors. The SLAM coordinate system corresponds to the coordinate system of the SLAM system 14. The SLAM coordinate system has preferably its origin in one of the SLAM sensors.

The AR display 15 is configured to display an AR visualization to the user wearing the HMD 10 overlaying the (real) environment seen by the eyes of the user. So, the AR visualization displayed in the AR display 15 augments the reality seen by the user through the HMD 10. Preferably, the AR display 15 allows to see the real environment of the HMD 10 without the need of any electronic means so that the AR visualization can be displayed over the real environment. The AR display 15 comprises preferably a transparent element arranged in the field of view of the user which allows the user to look through the transparent element to the see the real world. The AR display 15 is preferably configured to display on this transparent element the AR visualization. This can be done by a projector or some transparent display elements in the transparent element. However, it would also be possible to project the AR visualizations directly in the eye of the user or on the environment. Any AR display technology can be used for the AR display 15. In a less preferred embodiment, it is also possible to use a pass-through AR display in which the environment of the HMD is electronically displayed on the AR display. The AR coordinate system corresponds to the coordinate system of the AR display 15. The AR coordinate system has preferably its origin on the optical axis of the AR display 15, i.e. on the optical axis of the view of the user wearing the HMD 10.

Existing HMDs like the Microsoft HoloLens 1 (registered trademark), the Microsoft HoloLens 2 (registered trademark) or the Magic Leap One (registered trademark) could be used as hardware for the above-described HMD 10 programmed with the functions described in more detail below.

The augmented reality system according to the invention comprises the HMD 10 and a set of object markers 21.

Figure 2:
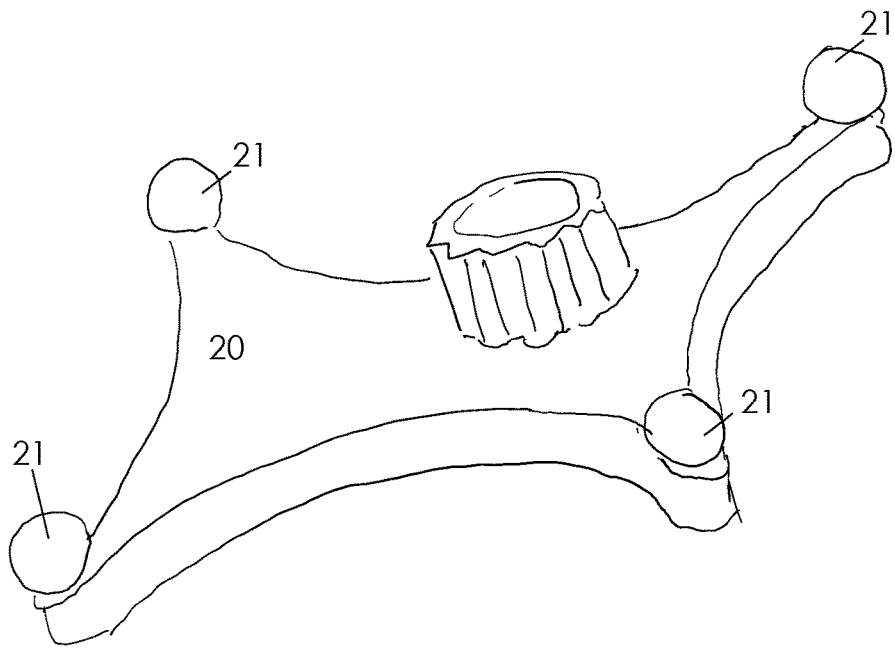
FIG. 2 shows an example object with object markers according to the invention.

The set of IR object markers 21 is arranged/arrangeable on an object which shall be tracked with the HMD 10. The IR object markers (short: markers) 21 are either actively emitting an IR light or reflecting IR light, e.g. from the IR light source 13. In a preferred embodiment, the markers 21 are reflecting IR light. Preferably, the markers 21 are retro-reflective markers. The markers 21 have preferably a spherical form. Due to the spherical form, its 2D representation in the IR image should correspond to a circle from all directions of view. However, also other forms of the markers 21 could be used. The set of markers 21 comprises at least four markers 21. Preferably, the at least four markers 21 are arranged in an asymmetric way on the object 20. This helps to retrieve the correct orientation of the object from the 3D positions of the markers 21 of the set of markers 21. The spatial/local relationship/arrangement between the markers 21 of the set of markers 21 arranged on the object 20 is known to the HMD 21 or stored in the HMD 21. This can be achieved by pre-stored spatial relationships of sets of markers 21 for standard objects 20. This can also be achieved by registering an object 20 as will be explained in more detail below. The object 20 is preferably a surgical tool like a drill, a catheter, an implant, etc. The surgical tool can be for example a surgical tool which is applied mainly in one direction of application along an application axis of the surgical tool. This can be a drill, a screwdriver, etc. FIG. 2 shows a patient locator as an example object 20 which is fixed on a part of the patient to detect with the HMD 20 the pose of the patient. The set of markers 21 are arranged in a fixed position on the object 20 so that the spatial relationship between the markers 21 of the set of markers 21 on the object 20 cannot change. Different objects 20 have preferably different spatial relationships between their markers 21 and/or different number of markers 21 so that the HMD 20 can detect from the spatial relationship and/or number of the markers 21 the (type of) object 20. The object 20 can also be part of the augmented reality system.

The markers 21 within a set of markers 21 are preferably labelled. That is that each marker 21 of the set of markers 21 has a different label. A label is an identifier for identifying the marker 21. The identifier or label is preferably just virtual, i.e. is not visible from the image of the marker 21 in the IR image of the IR camera 12. The label of each marker 21 can be determined based on the 3D spatial relationship of the set of markers 21. A set of four markers 21 can for example be labelled from 1 to 4.

Figure 4C:
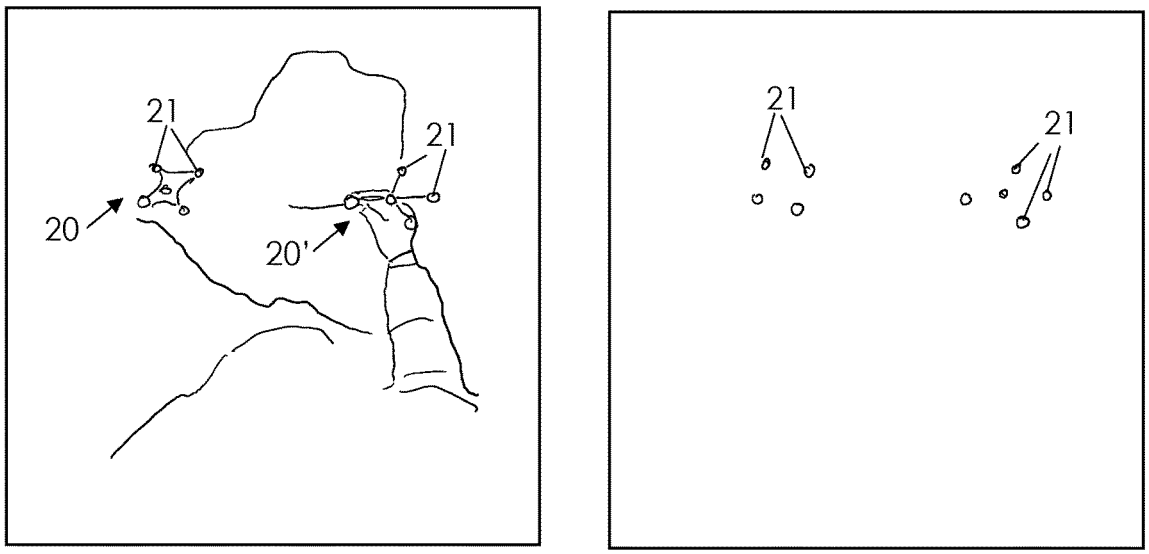
FIG. 4C is the IR image with the detected object pose.
Figure 4C:
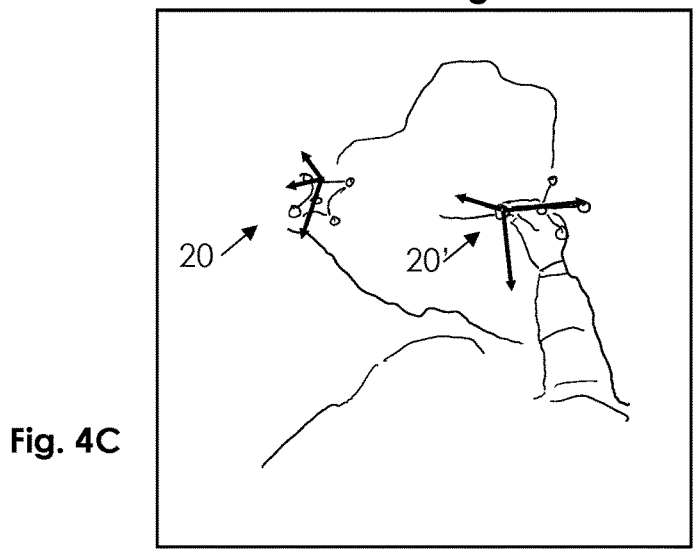

The system can also comprise two or more objects 20 to be tracked, each having a (different) set of markers 21 arranged on it. For example, the first object can be a patient locator fixed on the patient to detect the pose of the patient (or a part of the patient like a certain bone) having a first set of markers 21 arranged on it as shown for example in FIG. 2. For example, the second object can be a surgical tool having a second set of markers 21 on it. The second set of markers 21 has a different spatial arrangement/relationship of markers 21 compared to the first set of markers 21 so that the two objects can be distinguished in the same IR image by the spatial relationship of their markers 21. Thus, when the HMD 10 can track both objects 20 together, it is possible to track the relative position of the second object or the surgical tool with respect to the first object or the patient. This allows to guide the surgeon with the correct application position of the surgical tool with respect to the patient based on the relative pose of the two objects 20. FIG. 4A shows for example an IR image taken with the IR sensor 12 showing two objects 20. The first object 20 is a patient locator fixed with respect to the patient or the region of interest of the patient. The second object 20' is a surgical tool 20' for example a drill.

Before explaining the method according to the invention, some terms shall be clarified.

A pose according to the invention defines the three-dimensional position of the object 20 and the three-dimensional orientation of the object with respect to a coordinate system. Thus, the pose defines the "position" of the object in all six degrees of freedom.

A 3D position means a point in a three-dimensional space, i.e. a three-dimensional point in a coordinate system.

A 2D position means a pixel position in an image, normally in an IR image taken by the IR camera 12. The 2D position has preferably a sub-pixel precision.

A world coordinate system is the three-dimensional coordinate system of the (non-moving) environment surrounding the HMD 10.

An HMD coordinate system is any three-dimensional coordinate system which is fixed with respect to the HMD 10. The HMD coordinate system could be the IR sensor coordinate system, the AR coordinate system or the SLAM coordinate system or any other coordinate system fixed with the HMD 10. The IR sensor coordinate system, the AR coordinate system and/or the SLAM coordinate system might have different origins and/or orientations but have a fixed relationship among each other due to their fixed arrangement in the HMD 10. This allows to transform the pose in one HMD coordinate system into the pose in another HMD coordinate system.

Figure 5:
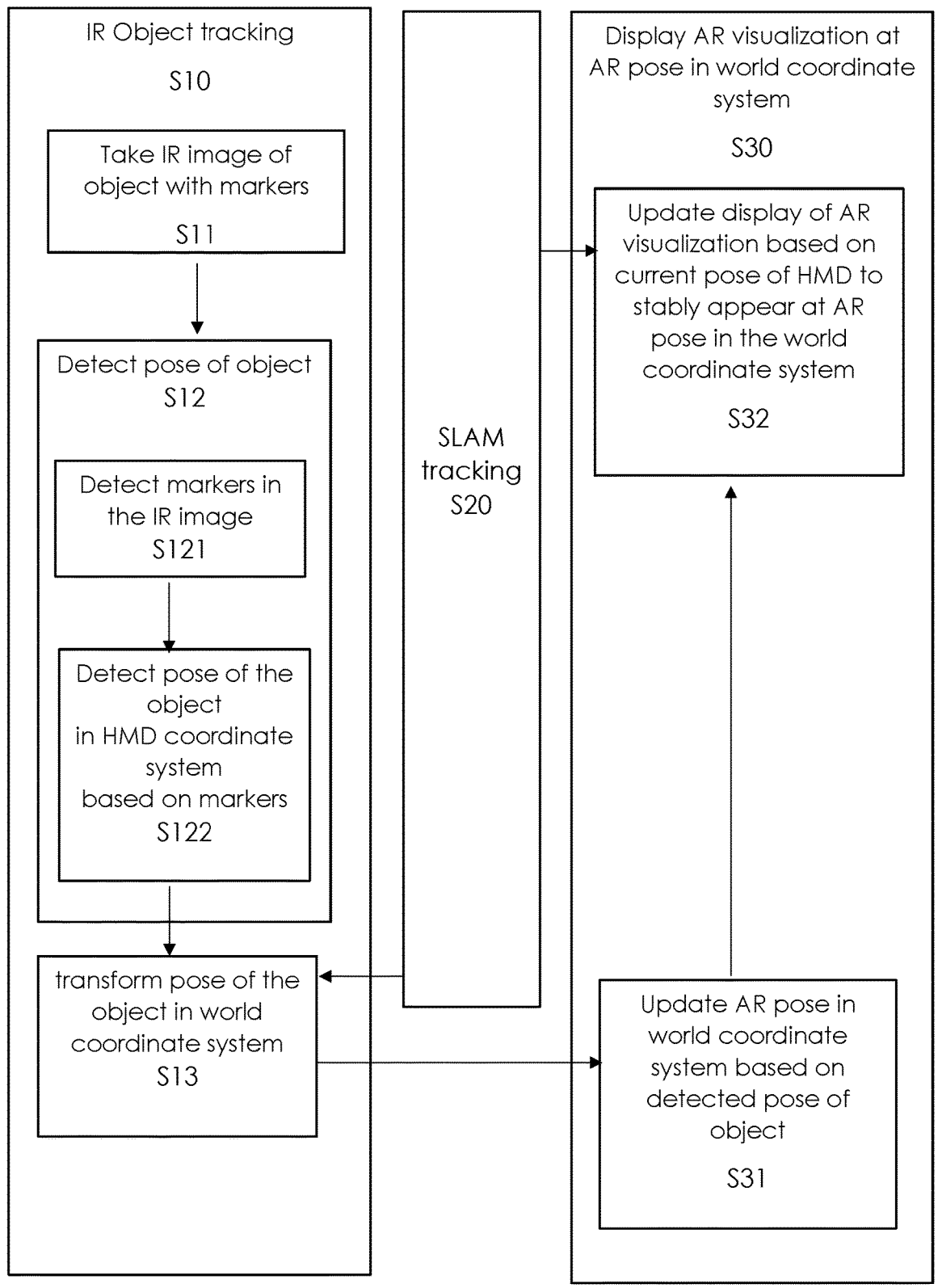
FIG. 5 describes a method according to the invention.

FIG. 5 shows schematically the principal steps of the method according to the invention to display an AR visualization with the HMD 10 at a certain location in the world coordinate system.

The method comprises three main steps or processings: the object detection S10, the SLAM S20 and the display of the AR visualization S30. Since the method needs to work in real-time, the three steps/processings work more or less in parallel with certain interactions between them.

In step/processing S20, the SLAM processing is performed. The SLAM processing computes based on the SLAM data received from the SLAM system 14 the 3D map of the environment surrounding the HMD 10 and the pose of the HMD in this environment/3D map. The 3D map of the environment is expressed in the world coordinate system. The point of origin (short: origin) of the world coordinate system is chosen as a point in the environment which is not moving. The origin and orientation of the world coordinate system could change from time to time, e.g. when the HMD 10 walks into a new environment. This is no problem as long as the pose of the HMD 10 in this environment is always chosen relative to the used world coordinate system. The pose of the HMD 10 in this environment is thus the pose of the HMD 10 or of the HMD coordinate system in the world coordinate system. The pose of the HMD 10 in the world coordinate system determined in each SLAM iteration is shortly also called HMD pose. The SLAM iterations are preferably periodically repeated, i.e. with fixed time differences between two consecutive SLAM iterations defined by the SLAM sampling rate. The SLAM sampling rate is for example larger than 40 Hz or than 50 Hz or than 60 Hz. However, it would also be possible to have non-periodic SLAM iterations. This step preferably comprises as well the receiving of the SLAM data from the SLAM system 14 based on which the SLAM processing is performed. The SLAM data are received preferably also at the SLAM sampling rate. That is each time new SLAM data is received from the SLAM system 14, a new HMD pose is determined based on the new SLAM data. However, it is also possible that the SLAM data are received more often than there are SLAM iterations, e.g. if the time for a SLAM iteration takes longer than the time between two SLAM data sampling times. Preferably, also the 3D map of the environment is updated based on the new SLAM data in each SLAM iteration. Thus, the step S20 is repeatedly, preferably periodically performed during the method of the invention and in parallel with the other steps S10 and/or S30. SLAM algorithms are well known and are thus not described in detail here. A standard SLAM algorithm and SLAM system as for example available in an off-the-shelf Microsoft HoloLens can be used.

In step S10, the IR object tracking is performed. The IR object tracking comprises the detection of the pose of the object in the world coordinate system at each iteration of the IR object tracking (short IR iteration). The IR object tracking is preferably performed based on a monocular IR tracking approach, i.e. the IR object detection in each IR iteration can be performed based on a single IR image taken in this IR iteration (contrary to a stereo image tracking approach which requires two simultaneously taken images of the environment from different view points). Subsequently, the steps performed in one IR iteration are exemplarily explained. If not otherwise specified, the subsequent explanation and terms refer to the ones of the IR iteration explained, i.e. the current IR iteration.

The steps of each IR iteration of the IR object tracking are performed continuously, preferably periodically, preferably with an object pose detection sampling rate. Preferably, between two subsequent detections of the object pose, one or a plurality of HMD poses are detected so that the HMD pose in the world coordinate system in step S20 is detected more often than the object pose in the world coordinate system in step S10. Preferably, the object pose detection sampling rate is lower than the SLAM sampling rate, i.e. in the same time period more SLAM iterations are performed than IR iterations. The object pose detection sampling rate is in this embodiment smaller than 50 Hz or than 40 Hz or than 30 Hz or than 20 Hz and/or is larger than 5 Hz, larger than 10 Hz, larger than 20 Hz.

In a first step S11 of the IR iteration, an IR image is taken/captured by the IR sensor 12 or is received in the processing means 11 from the IR sensor 12. The IR image taken shows an IR image of the field of view of the user wearing the HMD 10. The IR image is captured at the time of the IR iteration so that the pose of the object detected based on the IR image corresponds to the pose of the object at the time of the IR iteration and/or of capturing the IR image. Thus, the IR image shows all markers 21 which are present in the field of view of the user wearing the HMD 10. FIG. 4A shows an exemplary IR image taken by the IR camera 12. The IR image is continuously, preferably periodically taken/received. Preferably, the IR image is taken/received with an IR image sampling rate. Preferably, the IR image sampling rate is equal to the object pose detection sampling rate so that for each IR image obtained by the IR camera 12, the object pose detection step S12 is performed. However, it would also be possible to have a higher IR image sampling rate than the object pose detection sampling rate. In this case, the object pose detection step S12 would use the last IR image obtained in step S11. This can be for example the case, when sampling rate of the IR camera cannot be exactly adapted to the sampling rate of the object pose detection.

In a preferred embodiment, the IR light source 13 illuminates the field of view of the HMD 10, i.e. the field of view of the user wearing the HMD 10, with IR light before and/or while taking the IR image. This is especially important when the markers 21 are IR reflective markers. In case of actively IR light emitting markers, this can be avoided.

The IR image of the current IR iteration is taken by/received from the IR camera 12 is used for the IR object detection of the current IR iteration. The IR image of the current IR iteration corresponds normally to the last IR image taken by the IR image sensor to obtain the most up to date pose of the object in the current IR iteration. Preferably, the pose of the object 20 in the world coordinate system in the IR iteration is determined based on the IR image and on the pose of the HDM in the world coordinate system received from the SLAM processing S20. Preferably, the pose of the object 20 in the world coordinate system is determined based on the IR image, on the pose of the HMD10 in the world coordinate system received from the SLAM processing S20 and on the knowledge of the spatial relationship of the markers 21 arranged on the object 20. Subsequently, the object pose detection based on the IR image in the IR iteration will be explained in more detail.

Figure 3:
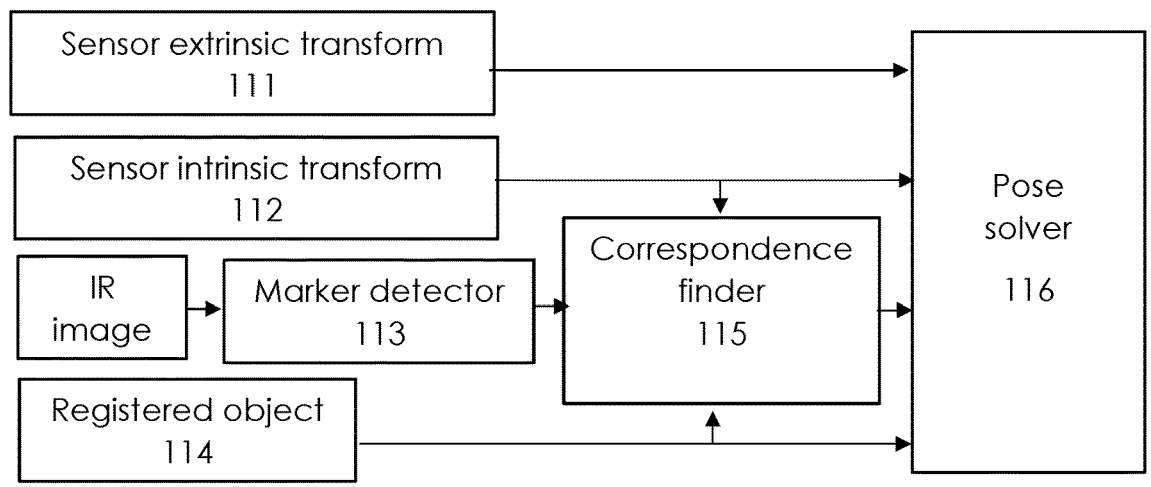
FIG. 3 shows a schematic diagram of the detection of the pose of the object according to the invention.

In step S12, the pose of the object 20 in the HMD coordinate system is determined based on the IR image taken in step S11. FIG. 3 schematically shows the architecture of such an object pose detection in the HMD coordinate system S12.

In step S121, the markers 21 are detected in the IR image. The markers 21 detected in the IR image in step S121 can be described as candidate markers 21 which fulfill certain requirements to be considered as candidate marker 21. The requirements can depend on the luminosity (above a certain threshold), the size and/or the form of the (candidate) marker 21 in the IR image. In an optimal case, the same number of markers 21 are detected in the IR image as the set of markers 21 of the object 20. However, it is also possible that a lower number of markers 21 are detected, if some of the markers 21 are occluded e.g. by the specific pose of the object 20 itself or by another object in front of the object 20 to be detected. It is further possible that a higher number of (candidate) markers 21 is detected, if something else than the IR object marker 21 of the set of markers 21 emits or reflects IR light which leads to a false positive candidate marker 21 or if more than one object 20 is detected in the IR image. Preferably, the (candidate) markers 21 in the IR image and their 2D positions in the IR image are detected in step S121. The IR image has preferably a 2D coordinate system expressed in pixels. A first dimension extends in the image plane in a first direction, often called the x-axis or the row direction. A second dimension extends in the image plane in a second direction, often called the y-axis or the column direction. A 2D position of the IR image is a point in the IR image with two coordinates. The 2D position can also be expressed with a sub-pixel precision. Since the markers 21 emit or better reflect IR light and the IR image detect the intensity of IR light in the field of view, the markers 21 have a high IR intensity. So, one possible way to detect the markers 21 in the IR image is to detect all pixels above a certain IR light intensity as points of the markers 21. In addition, further algorithms can be used to avoid false positive points in the IR image with high IR intensity, for example that a number of neighboring pixels have as well a high IR light intensity. FIG. 4B shows for example a processed IR image of FIG. 4A showing only the pixels with an IR intensity above a certain threshold. The maximum intensity value of the IR image can be used as threshold, e.g. 8 bits=255. Preferably, a group of connected high-intensity pixels are considered to form a marker 21. In a preferred embodiment, the position of each marker 21 is detected based on the pixels associated to the same marker 21. In a preferred embodiment, the contour of a group of (connected) pixels defining one (or more) markers 21 detected in the IR image is used for detecting the markers 21 and/or for detecting the 2D position of the detected marker 21. The contour can be used to detect which group of pixels belong to a marker 21 or to two or more markers 21 at the same time. The contour can be filtered based on geometric criteria: area, aspect ratio, circularity, and hierarchy. This allows to detect which group of pixels are actually not markers 21 (false positives) and can be removed subsequently from consideration. This allows also to detect markers 21 being so close together in the IR image that they overlay each other. The contour of groups of pixels can further be used to detect the position of the marker(s) 21 related to the contour. Preferably, the form of the markers 21 projected on the IR image (here a circle) is fitted on each contour. This allows to determine the center of the marker 21, i.e. the 2D position of the marker 21 in the IR image with a high precision. Preferably, a two-dimensional (2D) Gaussian approximation is used to fit the circle on the contour. If two markers 21 were detected in the same group of pixels, two circles can be fitted on the group of pixels. The same holds obviously for more than two markers 21. For processing each group of pixels, preferably a bounding box including the group of pixels is used. Preferably, the bounding box is padded, e.g. with one or two pixels, before processing the bounding box of the group of pixels. This allows to detect the center of the marker in the IR image with a high precision. This is quite unusual as the use of fitting algorithms for marker detection is computationally rather intense and thus normally not used in real time image processing. However, it was found that this improves significantly the quality of pose detection. FIG. 3 shows the marker detector 113 which performs the described step S121. Many more additional or alternative algorithms exist to obtain a stable detection of IR markers 21 in the IR image. These alternative algorithms are state of the art and are not described in more detail here. However, it was found that these alternative state of the are algorithms perform less good than the described one.

In step S122, the pose of the object in the HMD coordinate system is determined/computed based on the markers 21 detected in the IR image, more precisely based on the 2D positions of the markers 21 in the IR image. Preferably, the pose of the object in the HMD coordinate system is determined/computed based on the markers 21 detected in the IR image and based on the known spatial relationship of the markers 21 in the set of markers 21 arranged on the object 20. Preferably, the pose of the object 20 is determined based on the 3D positions of the markers 21. The 3D positions of the markers 21 (or the pose of the object) in the HMD coordinate system are (is) determined based on the 2D positions of the markers 21 in the IR image. Preferably, in this step S122, the IR sensor coordinate system is used as HMD coordinate system. Preferably, the 3D positions of the markers 21 in the HMD coordinate system are determined based on the 2D positions of the markers 21 in the IR image and based on the known camera parameters of the IR camera 12. In the following, one preferred way to detect the pose of the object in the HMD coordinate system is determined/ computed based on the markers 21 detected in the IR image.

In a preferred embodiment, this is done by a correspondence detection algorithm. The correspondence detection algorithm is realized in the correspondence finder 115 in FIG. 3. A correspondence detection algorithm determines for each (candidate) marker 21 detected in the IR image the corresponding marker 21 of the object 20 in the set of markers 21. In other words, the correspondence detection algorithm relates each marker 21 detected in the IR image to a corresponding marker 21 of the object to be detected and/or of the set of markers 21. Thus, it identifies for each detected marker 21 the corresponding label of the marker 21 of the set of markers 21 of the object 20. Once, the correspondences of the markers 21 in the 2D image with respect to the corresponding markers 21 of the set of markers 21 of the object 20 are known, the exact 3D positions of all markers 21 in the HMD coordinate system (more precisely in the IR sensor coordinate system) can be calculated by the pose solver 116 based on their 2D positions in the IR image, their correspondences, the spatial relationship of the set of markers 21 of the registered object 114 and based on the camera model 112. The camera model 112 and the spatial relationship of the set of markers 21 (registered object 114) are stored in the HMD 10 to perform the described computations. Normally, the correspondences of at least 4 (candidate) markers 21 in the IR image must be detected to find a solution in the pose solver 116. However, when the prior pose of the object detected in the prior IR iteration (or one of the recent prior IR iterations) is available, also the correspondences of only 3 (candidate) markers 21 in the IR image are sufficient to find a solution in the pose solver 116. The pose solver is preferably based on a PnP algorithm with n corresponding to the (candidate) markers 21 in the IR image for which correspondences were found in the correspondence finder 115. Preferably, the pose solver 116 uses in addition the prior pose of the object in the HMD coordinate system of the prior IR iteration or a recent one of the prior IR iterations to detect the pose of the object in the HMD coordinate system for the current IR iteration. If the HMD coordinate system mainly used in the HMD is not the IR sensor coordinate system, the sensor extrinsic transform 111 is used to transform the pose of the object in the IR sensor coordinate system into the HMD coordinate system, e.g. the AR coordinate system.

In a preferred embodiment, in step S122 or in the correspondence finder 115, two different cases are distinguished: if a recent prior pose of the object is available, the correspondence between the markers 21 in the IR image and the markers 21 in the set of markers 21 is determined based on a first correspondence algorithm, and, if no recent prior pose of the object is available, the correspondence between the markers 21 in the IR image and the markers 21 in the set of markers 21 is determined based on a second correspondence algorithm. A recent prior pose of the object is considered a pose of the object not older than a certain time threshold. The time threshold could be expressed in a time, e.g. not older than a second or half a second or 0.1 seconds, or in a number of IR iterations, e.g. 5 IR iterations. Normally, when in the prior step S12 the pose of the object was detected, the first correspondence algorithm is performed. However, also when maybe the pose of the object was not detected in the last steps S12, maybe because the user looked for a very short time in the other direction or because the object to be detected was covered, the first correspondence algorithm can still be used, if the last pose of the object determined was not older than the certain time threshold, because the likelihood that the object 20 has moved is low. Otherwise, if the last pose of the object is not available or older than the certain time threshold, the second correspondence algorithm is used.

The first correspondence algorithm uses the information from a prior IR iteration, more precisely of the last IR iteration in which the pose of the object was (successfully) determined. Preferably, the first correspondence algorithm determines (the labels or the correspondences of) the markers 21 detected in the IR image corresponding to the set of markers 21 of the object 20 based on the 2D positions of the markers 21 in the IR image of the prior IR iteration. Preferably, the first correspondence algorithm determines (the labels of) the markers 21 detected in the IR image of the current IR iteration (current IR image) corresponding to the set of markers 21 of the object 20 based on a distance measure between the 2D positions of the markers 21 in the current IR image and the 2D positions of the markers 21 detected in the IR image of the prior IR iteration (prior IR image). Preferably, for each marker 21 detected in the current IR image, the distance measure with respect to the 2D position of all markers 21 in the IR image in the previous step are calculated. The best correspondence can then be calculated by a Hungarian assignment algorithm using the distances of all possible assignments as cost function. As a distance measure the square distance could be used. The correspondence assignment is based preferably further on a threshold distance, i.e. the correspondence between a marker 21 detected in the current IR image with a corresponding marker 21 of the set of markers 21 is only accepted, if its distance in the 2D image space between the 2D position of its current image and the 2D position of its previous IR image is smaller than the threshold distance. The threshold distance can depend on the magnitude of its image space velocity, i.e. the velocity of this marker 21 in the IR image. This velocity can be determined from the movement of this marker 21 over at least two prior IR iterations. For a successful correspondence detection, it is necessary that the correspondence for at least three markers 21 is found. If the correspondence is found only for less than three markers 21, the method goes back to step S11 to take a new IR image and perform a new object pose detection step S12, i.e. performs a new IR iteration of IR object tracking S10. However, it is also possible that in this case the second correspondence algorithm is performed. It is also possible that only, if in a certain number of consecutive IR iterations, the first correspondence algorithm failed, the second correspondence algorithm is performed.

The second correspondence algorithm uses a PnP algorithm to find the correspondences. The second correspondence algorithm projects a (sub)set of n markers 21 (with the spatial relationship of the n markers 21 provided by the set of markers 21) having a plurality of different poses in the HMD coordinate system into the IR image (using the camera model 112) to find the pose of the (sub)set of n markers 21 coming closest to the markers 21 detected in the IR image. Normally n being four or bigger is used or n=3 is used performing the P3P algorithm for all permutations of three markers 21 within the set of markers 21 of the object 20. However, this is computationally intense and requires worthy time and power. This is why it is proposed to use a predefined subset of three markers 21 of the set of markers 21 of the object for the P3P algorithm. The predefined sub-set of three markers 21 is selected such that the three markers 21 selected among the markers 21 of the set of markers 21 form the triangle with the largest area (with respect to the area of the triangles formed by all other permutations of three markers 21 of the set of markers 21). The second correspondence algorithm is an iterative algorithm which is configured in each correspondence iteration to perform the following steps.

In a first step of the correspondence iteration, a candidate correspondence set of three markers 21 detected in the IR image having candidate correspondences with the three markers 21 of the predefined sub-set of three markers 21 is defined. The candidate correspondence set of the current correspondence iteration is new with respect to previous candidate correspondence sets, i.e. is different to any correspondence set of previous correspondence iterations.

In a second step of the correspondence iteration, a P3P algorithm is performed to determine the (best) pose of the predefined sub-set of three markers 21 in the HMD coordinate system fitting on the 2D positions and correspondences of the candidate correspondence set. This pose of the predefined sub-set of three markers 21 results in the 3D positions of the three markers 21 of the predefined sub-set in the HMD coordinate system.

In a third step of the correspondence iteration, the 3D positions of the remaining ones of the set of markers 21 missing in the sub-set of three markers 21 are determined based on the determined pose of the predefined sub-set (or based on the 3D positions of the three markers 21 of the predefined subset in the HMD coordinate system) (and based on the spatial relationship of the markers 21 in the set of markers 21).

In a fourth step of the correspondence iteration, the 3D positions of the remaining ones of the set of markers 21 are projected into the IR image (based on the IR camera model 112).

In a fifth step of the correspondence iteration compare the 2D positions of the markers 21 detected in the IR image with the 2D positions of the markers 21 obtained by the projection into the IR image and/or obtained by the P3P algorithm resulting in a comparison measure. The comparison measure depends preferably on the distances between the 2D positions of the markers 21 detected in the IR image and their corresponding markers 21 of the set of markers 21 projected from the pose in the HMD coordinate system (of the third step) project into the IR image. This comparison measure could be for example based on the sum of the distances or the sum of the squared distances. The comparison measure indicates thus the detection error of the pose in the correspondence iteration.

The second correspondence algorithm determines the correspondences between the markers 21 in the IR image of the current IR iteration and the markers 21 of the set of markers 21 based on the comparison measure of the different correspondence iterations. The second correspondence algorithm can go through all correspondence iterations for all possible permutations of associating/corresponding the markers 21 detected in the IR image to the three markers 21 of the predefined sub-set and select then the correspondence set with the comparison measure with the best quality, e.g. with the lowest error or distance measure. It is also possible to stop the second correspondence algorithm once a correspondence set has been found which fulfils a certain quality condition, e.g. the comparison measure is below a certain quality threshold. The present algorithm preferably performs the P3P algorithm only on the pre-defined sub-set of three markers 21 without performing the P3P algorithm on any of the other sub-sets of three markers 21. However, in some embodiments, it could be possible to perform the P3P algorithm on a second sub-set of three markers 21, e.g. when the first sub-set of three markers 21 did not result in a solution. Different than in the state of the art, the P3P algorithm is not applied on all permutations of three markers 21 of the set of markers 21.

Other correspondence algorithms than the described first and/or second correspondence algorithms can be used. It is also possible to use other algorithms to detect the pose of the object in the HMD coordinate system based on the 2D positions of the (candidate) markers 21.

In step S13, the pose of the object in the world coordinate system of the IR iteration is determined based on the pose of the object in an HMD coordinate system of the IR iteration and based on the pose of the HMD 10 in the world coordinate system determined in the SLAM tracking. The pose of the HMD 10 in the world coordinate system allows to transform the pose of the object 20 from the HMD coordinate system into the world coordinate system. The HMD pose used for this transformation is preferably the HMD pose calculated based on the SLAM data sensed at the time when the IR image was taken. This is preferably the HMD pose of the SLAM iterations being more or less contemporaneous with the IR iteration, more precisely contemporaneous with the capture time of the IR image of the IR iteration. This is normally the last HMD pose of the last SLAM iteration.

The object detection processing/step was explained with respect to one object. In case, two or more objects 20 are present, the steps S122 and S13 are performed for each object which needs to be detected. This allows to determine from the same IR image of the IR camera 12 the pose of two or more objects. If the set of IR object markers 21 of the first object 20 and the set of IR object markers 21 of the second object 20' are arranged in different IR image regions, they can be grouped into two distinct groups of IR object markers detected in the IR image. In this case, the steps S122 and S13 can be performed first with only the first group of IR object markers detected in the IR image to detect the pose of a first one of the two objects 20, 20' and second with only the second group of the IR object markers detected in the IR image to detect the pose of the second one of the two objects 20, 20'.

In AR display processing S30, an AR visualization is displayed on the AR display such that the AR visualization appears on an AR position or an AR pose in the world coordinate system.

The AR position or the AR pose in the world coordinate system depends on the pose of the object in the world coordinate system of step S13. Since the pose of the object in the world coordinate system is detected newly in each IR iteration, the AR display processing S30 updates the AR visualization in step S31 to appear on the new AR pose/position depending on the new pose of the object 20 in the world coordinate system of the current IR iteration. Thus, each time a new pose of the object 20 in the world coordinate system is available, the AR visualization is redisplayed to appear on the new AR pose/position depending on the new pose of the object 20. Since the pose of the object in the world coordinate system is detected in the IR object tracking with a very high precision, the AR visualization can be displayed with a very high precision.

Until the pose of the object of the next IR iteration is available, the displaying of the AR visualization is updated based on the HMD poses in the world coordinate system obtained in the SLAM tracking such that the AR visualization is displayed stably at the AR position or AR pose in the world coordinate system of the current IR iteration. Since the latency of the IR object tracking is higher than in the SLAM tracking, the AR visualization could jump due to movements of the HMD 10 with respect to the world coordinate system between two IR iterations. This is avoided by updating in step S32 the AR visualization such that the AR visualization remains displayed stably at the AR position/pose computed in the step S31 of the current IR iteration using the HMD poses determined in the meanwhile in the SLAM tracking S20. Since a plurality of HMD poses is determined between two subsequent IR iterations, the AR visualization displayed on the AR display to appear on the AR position/pose is updated with the plurality of HMD poses obtained in the meanwhile to keep the AR visualization displayed stably at the AR pose/position. Even if the HMD pose tends to have a large error due to the accumulation of errors over time, the errors accumulate only during the short time between two subsequent updates of the AR pose/position based on the new pose of the object of S13, i.e. during the short time between two subsequent IR iterations. Thus, the correction of the AR visualization display based on the HMD pose of the SLAM tracking allows to smoothen the display of the AR visualization using the low latency of the SLAM algorithm without the disadvantage of the low precision of the SLAM algorithm, because the AR pose is updated each IR iteration by the precise pose of the object in the world coordinate system from the IR object tracking S10.

If in the IR object tracking, two or more objects 20 are tracked, the AR visualization or its AR pose/position can depend on the pose of the first object and the pose of the at least one second object. In this case, the AR visualization could comprise a first AR visualization at a first AR pose/position depending on the pose of the first object detected and a second AR visualization at a second AR pose/position depending on the pose of the second object detected.

AR visualization is preferably a medical information or surgical information displayed at an AR position/pose depending on the pose of the patient (i.e. on the pose of a IR tracked patient locator fixed with respect to the patient) and/or depending on a pose of a surgical/medical tool detected based on the markers 21 arranged on the surgical/medical tool. The surgical/medical information is preferably one or more of: medical 3D imaging data of the patient overlaying the patient at the correct pose, a surgical/medical target region showing where and/or in which orientation to apply a surgical/medical intervention, and a target pose of the surgical/medical tool for optimal surgical/medical application. Medical 3D imaging data can be also composed of a plurality of 2D imaging data with their corresponding spatial relationship. In one embodiment, the surgical/medical tool has an application axis for its main application (like a drill) and the AR visualization displays the extension of the application axis in the application direction so that the surgeon/medical stuff can see the trajectory of the surgical/medical tool, when applied in this pose on the patient along the application axis. If the AR visualization displays further the 3D imaging information of the patient on the patient based on the detected pose of the patient locator, the surgeon can control the trajectory of the surgical tool before starting its application. Examples of surgical/medical tools whose main application is along an application axis are: a drill with the application axis being the drill axis, a needle or any medical device with a needle with the application axis being the needle, a probe like an ultrasound probe, an invasive electrode. The medical tool is preferably a tool whose application involves an invasive intervention in the body of the patient. The AR visualization can then help to correctly apply the invasive intervention. However, also noninvasive medical tools can be used as medical tools like a pointer to plan maybe an intervention.

In a preferred embodiment, the method of the invention is initialized by defining the object(s) to be detected. This can be done for example by selecting the object(s) to be detected from a list of previously registered objects 20 in the HMD 10. For each registered object 20, the HMD 10 stores at least the spatial relationship of the set of markers 21 of the object 20. Preferably, further details of the object 20 like its 3D form is stored in the registered object 20. However, it is also possible to register new objects 20 in the list of registered objects 20 as will be explained in more detail below. Alternatively, the object(s) 20 present in the IR image can be also automatically detected by the HMD 10. This can be done also based on the set of markers 21 detected in the IR image or alternatively or additionally, with the help of other sensors like a 3D camera of the HMD 10. For example, a priority list of the most likely objects present in the IR image can be created based on the 3D image taken by a 3D camera of the HMD in the zone of the markers 21 detected in the IR image with a precision verification of the identity and pose of the object 20 by the IR markers 21 detected in the IR image. However, by selecting manually the objects 20 to be detected, this identification processing is not necessary, and the process can be accelerated. Even if it is preferred that the objects 20 are stored/pre-registered in the HMD 10, it is also possible to register an object 20 each time the method of the invention is initialized. It is also possible to register the objects 20 (instead of a generic list of all possible objects) in special AR programs which define the object(s) 20 to be detected and the AR visualizations to be displayed with respect to the detected object(s) 20.

The currently proposed HMD 10 with on-board processing and an inside-out tracking allows to have everything needed in the HMD 10 itself, except obviously the object markers arranged on the object to be detected. Thus, clutter is reduced in the operating room, as it does not rely on external tracking devices. As the current set-up is portable (head mounted device+medical instrumentation), it can also be used outside of the operating room, e.g. in the intensive care unit; where surgical navigation equipment is typically not available. While existing solutions with a similar hardware capacity reach only precision for displaying the AR content of around a centimeter, the present invention manages to obtain a precision of the displayed content of below 5 millimeters (mm), normally also below 3 mm with respect to the correct position in the real environment. In a prototype with a standard Microsoft HoloLens reprogrammed based on the described method, a precision of the displayed content of below 2 mm was achieved.

The invention was described for an HMD 10. However, the same system or method could be used with any other mobile, preferably wearable device. For example, instead of the HMD, a tablet can be used. The tablet can for example be fixed on the arm of a user or hold in the hand of the user. Like the HMD, the tablet or other electronic device would have the processing means 11, the IR image sensor 12, the SLAM system 14 and eventually the IR light source 13. The method to operate such other device would be equal than described in FIG. 5.

The term "iterative" shall include also "recursive" methods.

It should be understood that the present invention is not limited to the described embodiments and that variations can be applied without going outside of the scope of the claims.

The invention claimed is:

1. Augmented reality system comprising:
   a set of IR object markers attached in a known spatial relationship to an object to be detected,
   an HMD being a head mountable device,
   a SLAM system in the HMD configured to obtain continuously SLAM data,
   an AR display in the HMD configured to display an AR visualization to a user of the HMD overlaying the environment seen by the user when wearing the HMD,
   an IR image sensor in the HMD configured to capture an IR image of the environment of the HMD and to sense IR light from the IR object markers in the captured IR image,
   a processing means configured to perform a SLAM tracking, wherein the SLAM tracking detects an environment of the HMD in a world coordinate system and simultaneously detects the pose of the HMD in the world coordinate system using a SLAM algorithm, wherein the SLAM tracking iteratively at each SLAM iteration determines the pose of the HMD in the world coordinate system at the time of the respective SLAM iteration based on SLAM data received from the SLAM system at the time of the SLAM iteration;
   perform an IR object tracking comprising at each IR iteration of the IR object tracking:
      to capture with the IR image sensor an IR image at a time of the IR iteration;
      to detect IR object markers in the IR image of the IR iteration,
      to determine the pose of the object in an HMD coordinate system at the IR iteration based on 2D positions of the IR object markers detected in the IR image of this IR iteration and based on the known spatial relationship of the set of IR object markers, and
      to determine the pose of the object in the world coordinate system of the IR iteration based on the pose of the object in an HMD coordinate system of the IR iteration and based on the pose of the HMD in the world coordinate system determined in the SLAM tracking;
   display at each IR iteration the AR visualization on the AR display such that the AR visualization appears on an AR position or an AR pose in the world coordinate system depending on the pose of the object in the world coordinate system of the current IR iteration, wherein, until the pose of the object of the next IR iteration is available, the displaying of the AR visualization is updated based on the HMD poses in the world coordinate system obtained in the SLAM tracking such that the AR visualization is displayed stably at the AR position or AR pose in the world coordinate system of the current IR iteration.

2. The system according to claim 1, wherein the pose of the object in the HMD coordinate system is determined based on a correspondence algorithm which determines the correspondence between the IR object markers in the IR image and the IR object markers in the set of IR object markers, wherein the pose of the object in the HMD coordinate system is determined based on the 2D positions of the IR object markers in the IR image, based on the spatial relationship of the IR object markers in the set of IR object markers, and based on the correspondence between the IR object markers in the IR image and the IR object markers in the set of IR object markers.

3. The system according to claim 2, wherein the pose of the object in the HMD coordinate system is determined based on the following steps:
   when a recent prior pose of the object of one previous IR iteration is available, determine the pose of the object in the HMD coordinate system based on a first correspondence algorithm using the last pose of the object in the HMD coordinate system, and
   otherwise, determine the pose of the object in the HMD coordinate system based on a second correspondence algorithm.

4. The system according to claim 3, wherein the first correspondence algorithm determines the correspondence between the IR object markers in the IR image of the current IR iteration and the IR object markers of the set of IR object markers based on the distances between the 2D positions of the IR object markers of the IR image of the current IR iteration and the 2D positions of the IR object markers in the IR image of the one previous IR iteration for which the corresponding IR object marker in the set of IR object markers is known.

5. The system according to claim 4, wherein the first correspondence algorithm is a Hungarian assignment algorithm using said distances as cost function.

6. The system according to claim 5, wherein the correspondence between the IR object markers in the IR image of the current IR iteration and the IR object markers of the set of IR object markers determined by the Hungarian assignment algorithm is only accepted for those IR object markers whose distance between its 2D position of the IR object marker in the IR image of the current IR iteration and the 2D position of the IR object marker in the IR image of the one previous IR iteration is smaller than a distance threshold, wherein the distance threshold depends for each IR object marker in the IR image of the one previous IR iteration on the velocity of this IR object marker in the IR images of at least two previous IR iterations.

7. The system according to claim 4, wherein at least some of the 2D positions of the IR object markers in the IR image of the one previous IR iteration are determined from a projection into the IR image of the 3D positions of the IR object markers of the set of IR object markers in the HMD coordinate system obtained from the pose of the object in the HMD coordinate system of the one previous IR iteration.

8. The system according to claim 3, wherein the second correspondence algorithm is an iterative algorithm using a predefined sub-set of three IR object markers of the set of IR object markers, the second correspondence algorithm is configured in each correspondence iteration to:
define a candidate correspondence set of three IR object markers detected in the IR image having candidate correspondences with the three IR object markers of the predefined sub-set of three IR object markers, wherein the candidate correspondence set of the current correspondence iteration is different to any correspondence set of previous correspondence iterations;
perform a P3P algorithm to determine the pose of the predefined sub-set of three IR object markers in the HMD coordinate system based on the 2D positions and correspondences of the candidate correspondence set;
determine the 3D positions of the remaining ones of the set of IR object markers missing in the sub-set of three IR object markers determined based on the determined pose of the predefined sub-set;
project the 3D positions of the remaining ones of the set of IR object markers into the IR image;
compare the 2D positions of the IR object markers obtained by the projection into the IR image and/or by the P3P algorithm resulting in a comparison measure;
wherein the second correspondence algorithm determines the correspondences between the IR object markers in the IR image of the current IR iteration and the IR object markers of the set of IR object markers based on the comparison measure of the different correspondence iterations.

9. The system according to claim 8, wherein the first sub-set of three IR object markers are selected as the three IR object markers among the IR object markers of the set of IR object markers which form the triangle in between them with the largest area.

10. The system according to claim 8, wherein the second correspondence algorithm does not perform the P3P algorithm on other sub-sets of three IR object markers of the set of IR object markers.

11. The system according to claim 1, wherein the detecting of the IR object markers in the IR image of the IR iteration comprises to:
detect pixels with a high IR light intensity,
detect groups of connected pixels as IR object markers in the IR image,
detect the contour of the groups of pixels of the IR object markers in the IR image,
determine the 2D position of the IR object marker in the IR image with sub-pixel precision by fitting the form of the IR object marker in the IR image on the contour.

12. The system according to claim 1, comprising a second set of IR object markers attached in a known second spatial relationship to a second object to be detected, wherein the processing means is configured:
to determine the pose of the second object in an HMD coordinate system at the IR iteration based on 2D positions of the IR object markers detected in the IR image of this IR iteration and based on the known second spatial relationship of the IR object markers of the second set of IR object markers, and
to determine the pose of the second object in the world coordinate system of the IR iteration based on the pose of the second object in the HMD coordinate system of the IR iteration and based on the pose of the HMD in the world coordinate system determined in the SLAM tracking;
wherein the AR position of AR pose depends further on the pose of the second object in the world coordinate system.

13. The system according to claim 1, wherein the set of IR object markers are configured to reflect IR light, wherein the HMD comprises further an IR light source, wherein the IR light source emits IR light before and/or while capturing the IR image with the IR image sensor so that the IR image captured shows the IR light emitted by the IR light source and reflected by the IR object markers in the field of view of the HMD.

14. The system according to claim 1, wherein the object and/or second object is a medical tool for performing a medical operation on a patient and/or a patient locator to be fixed with respect to a patient for detecting the pose of the patient.

15. The system according to claim 1, wherein the object and/or second object is a patient locator to be fixed rigidly with respect to a patient, wherein the AR visualization at the AR position or AR pose contains medical information displayed with respect to the pose of the patient.

16. The system according to claim 12, wherein the medical information is one or more of: medical 3D imaging data of the patient overlaying the patient at the correct pose, a medical target region showing where and/or in which orientation to apply a medical intervention, and a target pose of a medical tool for optimal application of the medical tool.

17. The system according to claim 1, wherein the object and/or second object is a medical tool, wherein the AR visualization at the AR position or AR pose comprises a projected application zone of the medical tool, when applying the medical tool in the current orientation and/or at the current position.

18. The system according to claim 1, wherein the object is a patient locator to be fixed rigidly with respect to a patient, wherein the AR visualization contains at a first AR pose medical 3D imaging data of the patient overlaying the patient at the correct pose, wherein the second object is a medical tool applied along an application axis of the medical tool, wherein the AR visualization contains at a second AR pose the application axis of the medical tool in the direction of application of the medical tool based on the current pose of the medical tool.

19. Augmented reality HMD comprising:
- a SLAM system configured to obtain continuously SLAM data,
- an AR display configured to display an AR visualization to a user of the HMD overlaying the environment seen by the user when wearing the HMD,
- an IR image sensor configured to capture an IR image of the environment of the HMD and to sense IR light from IR object markers in the captured IR image,
- a processing means configured to
  - perform a SLAM tracking, wherein the SLAM tracking detects an environment of the HMD in a world coordinate system and simultaneously detects the pose of the HMD in the world coordinate system using a SLAM algorithm, wherein the SLAM tracking iteratively at each SLAM iteration determines the pose of the HMD in the world coordinate system at the time of the respective SLAM iteration based on SLAM data received from the SLAM system at the time of the SLAM iteration;
  - perform an IR object tracking comprising at each IR iteration of the IR object tracking:
    - to capture with the IR image sensor an IR image at a time of the IR iteration;
    - to detect IR object markers in the IR image of the IR iteration,
    - to determine the pose of the object in an HMD coordinate system at the IR iteration based on 2D positions of the IR object markers detected in the IR image of this IR iteration and based on a known spatial relationship of a set of IR object markers attached to an object to be detected, and
    - to determine the pose of the object in the world coordinate system of the IR iteration based on the pose of the object in an HMD coordinate system of the IR iteration and based on the pose of the HMD in the world coordinate system determined in the SLAM tracking;
  - display at each IR iteration the AR visualization on the AR display such that the AR visualization appears on an AR position or an AR pose in the world coordinate system depending on the pose of the object in the world coordinate system of the current IR iteration, wherein, until the pose of the object of the next IR iteration is available, the displaying of the AR visualization is updated based on the HMD poses in the world coordinate system obtained in the SLAM tracking such that the AR visualization is displayed stably at the AR position or AR pose in the world coordinate system of the current IR iteration.

20. Augmented reality method comprising:
- receiving continuously from a SLAM system in an HMD SLAM data and performing a SLAM tracking, wherein the SLAM tracking based on the SLAM data detects an environment of the HMD in a world coordinate system and simultaneously detects the pose of the HMD in the world coordinate system using a SLAM algorithm, wherein the SLAM tracking at each SLAM iteration determines the pose of the HMD in the world coordinate system at the time of the respective SLAM iteration based on SLAM data received from the SLAM system at the time of the SLAM iteration;
- performing an IR object tracking comprising at each IR iteration of the IR object tracking:
  - to receive from an IR image sensor in the HMD an IR image captured at a time of the IR iteration;
  - to detect IR object markers in the IR image of the IR iteration,
  - to determine the pose of the object in an HMD coordinate system at the IR iteration based on 2D positions of the IR object markers detected in the IR image of this IR iteration and based on a known spatial relationship of a set of IR object markers attached to an object to be detected, and
  - to determine the pose of the object in the world coordinate system of the IR iteration based on the pose of the object in an HMD coordinate system of the IR iteration and based on the pose of the HMD in the world coordinate system determined in the SLAM tracking; and
- displaying at each IR iteration an AR visualization on an AR display in the HMD such that the AR visualization appears on an AR position or an AR pose in the world coordinate system depending on the pose of the object in the world coordinate system of the current IR iteration, wherein, until the pose of the object of the next IR iteration is available, the displaying of the AR visualization is updated based on the HMD poses in the world coordinate system obtained in the SLAM tracking such that the AR visualization is displayed stably at the AR position or AR pose in the world coordinate system of the current IR iteration.

* * * * *